United States Patent [19]

Cairncross et al.

[11] Patent Number: 5,356,751

[45] Date of Patent: Oct. 18, 1994

[54] METHOD AND PRODUCT FOR PARTICLE MOUNTING

[75] Inventors: Allan Cairncross, Hockessin, Del.; Ulrich Klabunde, West Chester, Pa.

[73] Assignee: E. I. du Pont de Nemours & Company, Wilmington, Del.

[21] Appl. No.: 173,258

[22] Filed: Dec. 27, 1993

Related U.S. Application Data

[63] Continuation of Ser. No. 923,128, Jul. 31, 1992, abandoned.

[51] Int. Cl.$^5$ .............. G03F 7/34; G03F 7/28; G02B 21/34
[52] U.S. Cl. .................... 430/253; 430/144; 430/291; 359/396; 359/397; 359/398
[58] Field of Search ............ 359/396, 397, 398; 430/144, 158, 253, 291

[56] References Cited

U.S. PATENT DOCUMENTS

| | | | |
|---|---|---|---|
| 2,695,244 | 11/1954 | Fountain . | |
| 2,760,863 | 8/1956 | Plambeck | 430/306 |
| 3,380,831 | 4/1968 | Cohen et al. | 430/288 |
| 3,573,918 | 4/1971 | Chambers et al. | 430/254 |
| 3,649,268 | 3/1972 | Chu et al. | 430/291 |
| 3,661,576 | 5/1972 | Crary | 430/288 |
| 3,736,042 | 5/1973 | Mackovits et al. | 359/398 |
| 3,887,371 | 6/1975 | Baker | 430/29 |
| 4,011,350 | 3/1977 | Markovits et al. . | |
| 4,174,216 | 11/1979 | Cohen et al. | 430/257 |
| 4,263,385 | 4/1981 | Pampalone . | |
| 4,282,308 | 8/1981 | Cohen et al. | 430/271 |
| 4,294,909 | 10/1981 | Lee | 430/270 |
| 4,356,252 | 10/1982 | Lee | 430/270 |
| 4,683,190 | 6/1987 | Sondergeld et al. | 430/281 |
| 4,948,704 | 8/1990 | Bauer et al. | 430/291 |
| 5,001,037 | 3/1991 | Matthews et al. | 430/291 |
| 5,071,731 | 12/1991 | Chen et al. | 430/271 |
| 5,093,221 | 3/1992 | Chen et al. | 430/257 |

FOREIGN PATENT DOCUMENTS

| | | |
|---|---|---|
| 0048478 | 3/1982 | European Pat. Off. . |
| 0415580 | 3/1991 | European Pat. Off. . |
| 2596676 | 10/1987 | France . |
| 59-81832 | 5/1984 | Japan . |
| 60-54195 | 11/1985 | Japan . |
| 1006587 | 10/1965 | United Kingdom . |
| 2125183 | 2/1984 | United Kingdom .......... 359/396 |

OTHER PUBLICATIONS

T. Allen, Particle Size Measurement (Chapman and Hall 1990) pp. 217-248.

E. N. Cameron, Chapter 9, Ore Microscopy, Wiley, N.Y., 1961.

Fang, et al., Appl. Phys. Lett. 55(14), 2 Oct. 1989, pp. 1433–1435.

Kaye, et al., Powder Technol., 4(1970/1971), pp. 203–213.

Kiederowski, Angew. Chem. Int. Ed. Engl. 30(1991) No. 7. pp. 822–823.

Patent Abstracts of Japan, vol. 14, No. 76 (M-14)(558) re JP,A,55-37341.

Derwent Abstract AN 70-80492R re SU 264,625.

*Primary Examiner*—Charles L. Bowers, Jr.
*Assistant Examiner*—Mark F. Huff

[57] ABSTRACT

The process and product are disclosed for mounting free-flowing particles, which employ a support having a support surface with an array of tacky areas which have a size and bonding strength suitable for adhesion of either one or two of said particles. In the process the particles flow across the support surface to allow particles to contact the tacky areas and adhere thereto. An array of mounted particles may thus be provided which has at least 50% singly or doubly mounted particles.

19 Claims, 2 Drawing Sheets

METHOD AND PRODUCT FOR PARTICLE MOUNTING

This is a continuation of application Ser. No. 07/923,128 filed Jul. 31, 1992, now abandoned.

FIELD OF THE INVENTION

This invention relates to mounting particles, and more particularly to a method and product for mounting particles in an array.

BACKGROUND OF THE INVENTION

The analysis of small particles is often accomplished using microscopy. Through microscopy, the properties of individual particles can be observed and measured. Given the normally small number of particles actually analyzed relative to the number of particles in the bulk of the material being analyzed by microscopy, sampling methods and sample preparation are of utmost importance to the success of the method. It is recognized that the preparation of a slide containing a uniformly dispersed, representative sample is a particularly difficult problem, and the final result often depends more on the skill of the operator than the procedure itself. See, e.g., T., Allen, Particle Size Measurement (Chapman and Hall, 1990) pages 217-248. Methods include casting in a plastic-like material and immobilization in gelatin. There remains a need for improved particle mounting techniques.

SUMMARY OF INVENTION

A process is provided in accordance with this invention for mounting free-flowing particles in an array, having at least 50% singly or doubly mounted particles. This process comprises the steps of (a) providing a support surface having an array of tacky areas which have a size and bonding strength suitable for adhesion of either one or two of said particles; and (b) flowing said particles across the support surface to allow particles to contact the tacky areas and adhere thereto. This invention also provides a product for mounting free-flowing particles in an array. This product comprises a support having a support surface with an array of tacky areas which have a size and bonding strength suitable for adhesion of either one or two of said particles.

DETAILED DESCRIPTION OF THE INVENTION

This invention involves mounting free-flowing particles. Free-flowing particles are particles that do not stick to each other under mounting conditions. They do not clump. In other words, there is no substantial binding force to be overcome when separating a mass of said particles into separate discrete particles. Examples, of free-flowing particles include certain mineral grains, crystalline chemical products, salt and sugar granules, polymer particles, mechanically ground solids, pollen, spores, and seeds.

This invention provides a process for mounting free-flowing particles on a surface at predetermined locations (i.e., in an array). Typically the array will be a repeating pattern arrangement. The process of this invention involves providing a support surface having an array of tacky areas. Tacky areas are areas which have adhesive properties which enable them to form bonds immediately after they are brought into contact with free-flowing particles under low pressure (e.g., the weight of the particles). The tacky areas should have a size and bonding strength suitable for adhesion of free-flowing particles. The support surface may be virtually any surface which is sufficiently smooth (except for the tacky areas thereon) for free-flowing particles to flow thereover. Preferred supports for mounting particles for analysis by microscopy are generally, transparent and colorless and have a generally planar surface. Supports may advantageously comprise flat glass or plastic (e.g., microscope slides).

The tacky areas are sized sufficiently large to retain the desired number of particles. Typically, the tacky areas are small shapes (i.e., dots) from about 0.25 $\mu$m to 1000 $\mu$m (i.e., $2.5 \times 10^{-7}$ m to $1 \times 10^{-3}$ m), and for many embodiments are from about 10 $\mu$m to 300 $\mu$m. The tacky area shapes may be circular, square, rectangular, oval, or another shape suitable for particle retention. Generally, circular areas are preferred.

The bonding strength of the tacky area should also be suitable to retain the desired number of particles. Accordingly, the size and immediate contact bonding strength of the tacky areas are two controlling factors for determining the number of particles to be mounted. In accordance with this invention the tacky areas have a size and bonding strength suitable for adhesion of either 1 or 2 particles.

The spacing of the tacky areas in the array is important to avoid particles which are retained on one tacky area from touching particles which are retained on adjacent areas. Normally, for substantially symmetrical particles and circular dots, the tacky areas are separated, center to center, by at least about 3 times the diameter of the tacky area, and preferably at least about 5 times the diameter of the tacky area.

For many embodiments, particularly embodiments directed to particle analysis, the tacky areas have a size and bonding strength suitable for adhesion of only one particle, and are preferably spaced such that no particles touch. Typically, the areas are spaced such that they are separated, center to center, by at least two times the longest particle dimension. This facilitates the analysis of each particle while avoiding problems created by particle overlap and uncertainties involving the discreteness of particles. Normally, for embodiments where only one particle is to be retained per tacky area, the size of each tacky area is less than the particle size, and the areas are separated, center to center, by at least about three times the diameter of the tacky area. Most preferably the particle width is about 2 to 3 times the width of the tacky dot, and the separation of dots, center to center is at least about 5 times the dot diameter. Typically, for a tacky area having a particular size and bonding strength, there is an upper limit to the size and weight of particles, above which there is no substantial particle adherence, and there is a lower limit to the size and weight of particles which will adhere singly to each tacky area.

For embodiments where single particle attachment at each tacky center is preferred, the particle size range and particle shapes in the sample should be considered. A narrow size range works best for single particle attachment to a given size tacky dot. In the case when single particle attachment is optimized when the particle width is 2 to 3 times the width of the tacky dot, the ratio of the largest particle to the smallest in this optimum range, herein referred to as the particle size range ratio, is 3/2 or 1.5. Many particle samples have very large range ratios, in excess of 50. In these cases, the best results are obtained by separating the sample into size fractions, usually by sieving, where each fraction has a limited size range. A particle size range ratio of 3 is useful. A particle size range ratio of 1.5 is preferred.

In addition, the shape of the particles and the attachment selectivity of the process are important. Where the tacky dots are slightly recessed below the surface and attachment of the particles is selective, rough irregular crushed particles attach more readily and multiply occupy tacky dots more easily than rounded smooth particles. For crushed titania slag (e.g., Richards Bay Slag) single attachment occurs best when the particle width, as defined by the sieve opening that just passes the particle, is 3 or more times the tacky dot width. A size range of 3 to 4.5 times the tacky dot width works well. For rounded smooth ilmenite sand the preferred size range is 2 to 3.5 times the width of the tacky dot. It is believed that this difference occurs because the rough crushed mineral has three contact points when at rest on a surface and often attaches to tacky dots by points and edges along the perimeter of a blocky particle, whereas rounded particles have only one contact point and attach approximately near the center of the particle. As a result the attached rounded particle is more centered over the tacky dot and more effectively blocks it from further attachment, particularly by another rounded particles. A mixture of rounded and rough irregular blocky crushed particles therefore gives a combined preferred size range for single mounting of about 3.0 to 3.5 (most preferred about 3.5) times the size of the tacky dot.

For embodiments where two particles per tacky dot is preferred the particle width should be approximately equal to the width of the tacky dot. For rounded particles double occupancy per tacky dot dominates at particle sizes equal in width and less than the tacky dot. For rough irregular blocky crushed particles double occupancy occurs when the particles are roughly 1 to 2 times the width of the tacky dot.

A variety of methods may be employed to form an array of tacky areas on the surface. Preferably, the method used gives clearly defined tacky areas, and provides a support surface and a tacky array that are clean (i.e., no adhered foreign material). It is further preferred that the layer containing the tacky areas has transparent, clear, colorless, and flat smooth areas between the tacky areas and that the tacky areas all lie in the same plane. Preferred methods for generating an array of tacky areas on a surface include methods which utilize photoimaging. A number of photosensitive products such as Cromalin® Positive Film SN 556548, Cromatone® Negative Overlay Film SN 031372 and Cromalin® Negative Film C/N are available from E. I. du Pont de Nemours and Company. The first, Cromalin® Positive Film, is preferred for more rapid thorough non-selective attachment of particles, especially non-uniform mixed particle samples. The latter two, Cromatone® Negative Overlay Film and Cromalin® Negative Film C/N, are preferred for uniform particle samples or selective attachment of mixed particle Samples and for the long shelf life of their tacky array images. These and other photosensitive products are disclosed in U.S. Pat. Nos. 3,649,268, 4,174,216, 4,282,308, 4,948,704 and 5,001,037. Typically, an array of tacky areas may be formed by (1) providing an actinic radiation sensitive multilayer product comprising (i) a strippable cover sheet, (ii) a photoadherable layer, (iii) a tacky, nonphotosensitive contiguous layer receptive to particulate material, and (iv) a support layer, wherein said tacky layer is attached between said support layer and said photoadherable layer and the cover sheet is removably attached to the photoadherable layer prior to exposure to actinic radiation and is adhered to areas of the photoadherable layer which are exposed to actinic radiation; (2) exposing the radiation sensitive multilayer element to actinic radiation imagewise in the array pattern, and (3) stripping off the cover sheet removing the photoadherable layer in the areas exposed by the actinic radiation. There should be facile control of the adhesive areas with respect to size and placement. For the aforementioned photosensitive products the array pattern is first composed by manual or computer assisted design, and is usually transferred to a photographic film that is used as a phototool in contact with the photosensitive product and with strong ultraviolet light to pattern the tacky array in the photosensitive product. For the Cromalin® products, the photosensitive material would first be laminated to the clear support, usually microscope slides, and then exposed through the phototool to create the pattern. For Cromatone®, a clear plastic film support is provided with the product so that it may be exposed directly through the phototool. Other patterning methods include projection exposure and direct writing as in digital imaging using a laser output device. A variety of other positive and negative photosensitive compositions are known to produce tacky images. Phototackifiable compositions become tacky where struck by light and are exemplified by compositions described in U.S. Pat. Nos. 5,093,221, 5,071,731, 4,294,909, 4,356,252 and German Patent No. 3,514,768. Alternatively, tacky adhesive can be printed directly on the support such as in flexographic printing and other graphic arts printing or by a method such as ink jet printing.

Another technique for providing a support surface having an array of tacky areas involves attaching thin sheet material having an array of holes to an adhesive coated substrate. Examples of such sheet material include screen mesh or stencils wherein holes have been formed by, for example, laser ablation, punching, drilling, etching, or electroforming. Other methods for providing a support surface having an array of tacky areas include providing photoresist hole patterns on an adhesive coated substrate; screen printing or stencil printing adhesive onto a support; screen printing or stencil printing a tackifying agent onto a substrate; and electrostatically depositing a pattern of cold fine powder adhesive and heating the powder to achieve tackiness and melting of portions of a surface to provide tacky areas during the adhesion step (e.g., using direct heat or other means such as lasers).

The location of the adhesive area relative to the background non-adhesive area can vary according to the method employed to generate the array of tacky areas. If ink jet printing is employed, the adhesive area is above the plane of the surface. If phototackification is used, the adhesive area is coplanar with the non-adhesive area as is the case if positive Cromalin ® is used. Negative Cromalin ® and Cromotone ® yield adhesive areas that are below the plane of the non-adhesive area. Generally, the further the adhesive material is recessed in relation to the non-adhesive surface, the more likely size exclusion will occur, where no particles larger than the width at the tacky area recess, will attach. This effect becomes particularly pronounced as the tacky area recess approaches the width of the tacky area.

After the tacky areas are provided, the particles are caused to flow across the support surface to allow the particles to contact the tacky areas and adhere thereto. This may be accomplished easily and efficiently using a holder designed to mount the support and to expose the desired portion of the tacky array to the particles through a window or well in the holder (e.g., a polished sheet of metal having a window cut therein, and stops for positioning a support such as a microscope slide relative to the window). A representative sample of the free flowing particles can then be applied to the well in the holder, and the well can be sealed with a cover while the particles flow across and adhere to the tacky areas of the array. The holder may then be turned so that the array is on top, and gently tapped to shake off loosely attached particles; and the support with the populated array may be removed from the holder for analysis.

There are several ways that the particles can be flowed across the tacky dots. A low velocity method involves holding the array with the particles sitting on top of the array and tipping back and forth letting gravity flow the particles across the tacky dots. As particles attach, the attached particles restrict the flow of adjacent unattached particles making flow to the last open tacky dots more difficult. Slow tumbling can overcome this or alternatively, the array is completely covered from end to end with excess particles such that very little motion is needed to completely contact all dots with particles. This method gives the least selectivity in attachment and generally high populations of attached particles and generally is preferred.

A second method involves horizontal shaking of the support with a limited amount of particles on top. the particles tumble, slide, and bounce across the surface until attached. When the dots are small (say, about one third the width of the particles) attachment is difficult. Also, when particles are round or have flat smooth surfaces and in addition, the tacky dots are recessed as in Cromalin ® Negative Film, attachment is particularly difficult. If the shaking is vigorous, previously attached particles are knocked off upon impact by unattached particles. Otherwise, attached particles are not easily replaced by particles flowing over them.

A third method involves holding the slide with the tacky dot array in the holder upside down with the particle sample in the well below it and vertically above. Attachment can be rapid and tacky site occupancy high but selectivity of one particle shape over another can be very high. For example, in a 1:1 mixture of two differently shaped particles, a rough irregular blocky crushed mineral can have a ten-fold attachment preference over a rounded particle of the same size. Cubic sodium chloride crystals, for example, show a strong preference for corner attachment in vertical shaking. In general, selectivity of one particle type over another increases as the attachment velocity increases.

Selectivity is also influenced by the tackiness of the dot and accessibility of the dot to attachment. Negative Cromalin ® has slightly recessed tacky dots; whereas Cromalin ® Positive Film is more tacky and has more accessible tacky dots coplanar with the surface, and is more effective in attaching particles upon contact with little discrimination or selectivity according to shape.

For almost all particle attachments described in these embodiments the attachments are the result of kinetic control, not equilibrium. This is repeatedly shown by populating an array with one component of a particle mixture, then removing excess loose particles and adding particles of another component of the mixture and showing that no significant exchange occurs as the second particle is flowed over the occupied tacky dots under normal attachment conditions.

Having a precisely defined number of particles makes counting and analysis of the percent composition of the various particles easier and potentially more accurate. The precise location of particles in a regular array makes both manual and automated counting and analysis methods easier. The fact that each particle has a precise location, indexible by coordinates, facilitates follow up analyses by multiple methods.

Mounting free-flowing particles in a dispersed, semi-permanent manner as disclosed herein is useful in microscopic analysis, particularly where the spacing is of the mounted particles is suitable for automated image analysis. Moreover, mounting in a location specific manner facilitates relocation of each particle for analysis using multiple techniques. Mounting in an array of single particles also facilitates determination of whether a sample contains different materials, which are fused to each other, and how much of such fused materials are present.

One preferred application involves mounting particles for the microscopic assay of commercial ores. The method of the present invention can be used as a rapid assay of ore quality. A rapid estimate can be made of the number of particles of each separate mineral component of the ore and, thus, the percentage of each component present can be estimated.

In general, the method of the present invention can be used for particle sizes ranging from 0.25 $\mu$m to 2000 $\mu$m. The method is particularly suitable for analysis of grains (e.g., ore grains) of 5 $\mu$m to 800 $\mu$m.

This invention makes it possible to analyze mixtures accurately. If a broad range of particle sizes are present, preferably the sample is first separated into size fractions. Representative samples are split from each fraction and mounted on tacky dot arrays on slides using a non-selective attachment procedure and dot sizes such that predominantly single particles are attached to each center. The number of each type of particle is counted on the slide. For accurate composition of the fraction the number of particles must be adjusted for the weight per particle for each component. The weight per particle can be easily determined using the same size fraction of the pure component, mounting individual particles at each center of a preweighed tacky dot array, weighing the mounted particles and counting the number of occupied centers. Using a masked holder and a regular array pattern makes the mounting of a uniform number of particles each time possible. Alternatively, the imaging pattern applied to form the tacky array on the slide can be limited to a precise and absolutely reproducible number and pattern of dots, so that the number and pattern of attached particles is controlled.

This invention also provides a product for mounting free-flowing particles in an array, comprising a support surface having an array of tacky areas which have a size and bonding strength suitable for adhesion of a selected number of said particles. These products can be adapted for various uses including ore assays, quality control analysis of particulate raw materials and products, and gathering field samples and samples of airborne minerals such as spores, dust, or pollen.

Figure 1:
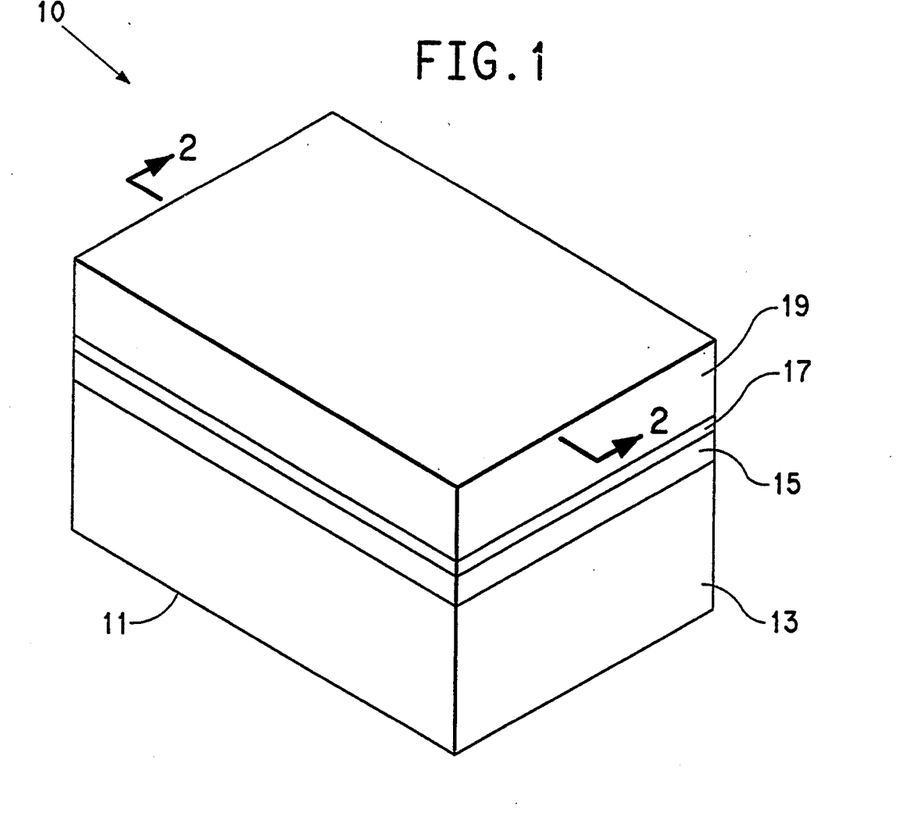
FIG. 1 is a perspective view of a product in accordance with this invention.
Figure 2:
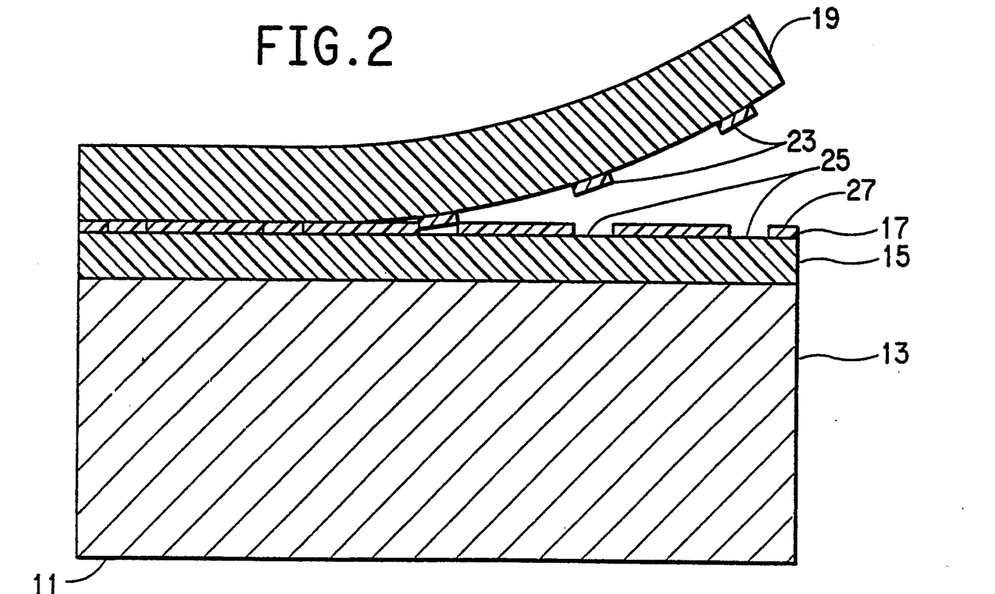
FIG. 2 is a section view of the product along section 2—2 of FIG. 1 through a row of photohardened portions thereof as the cover sheet is being removed.
Figure 3:
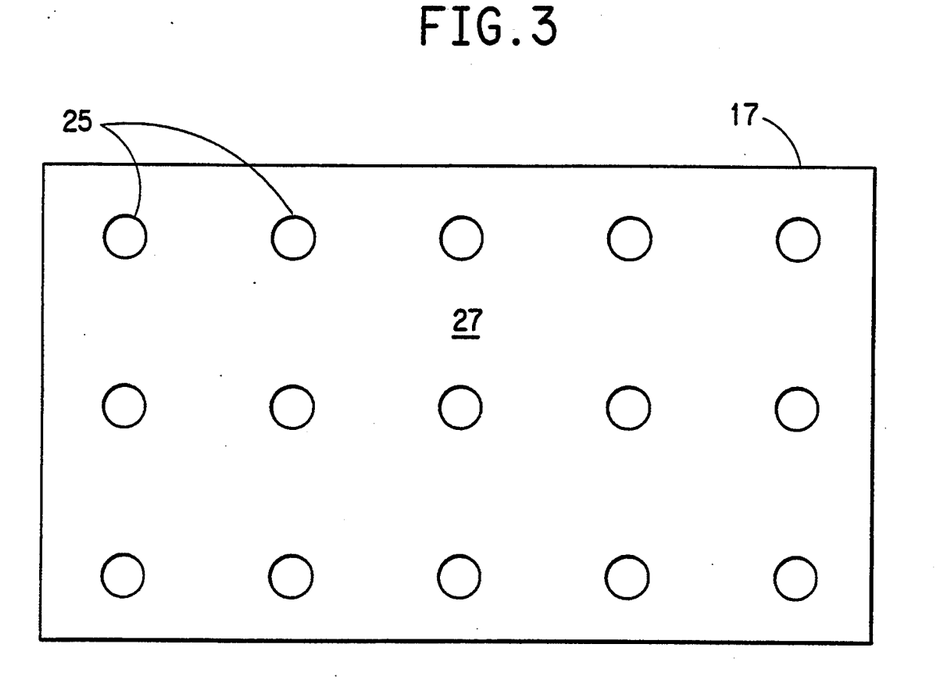
FIG. 3 is a plan view of the product of FIG. 1 with the cover sheet removed and the tacky areas exposed.
Figure 4:
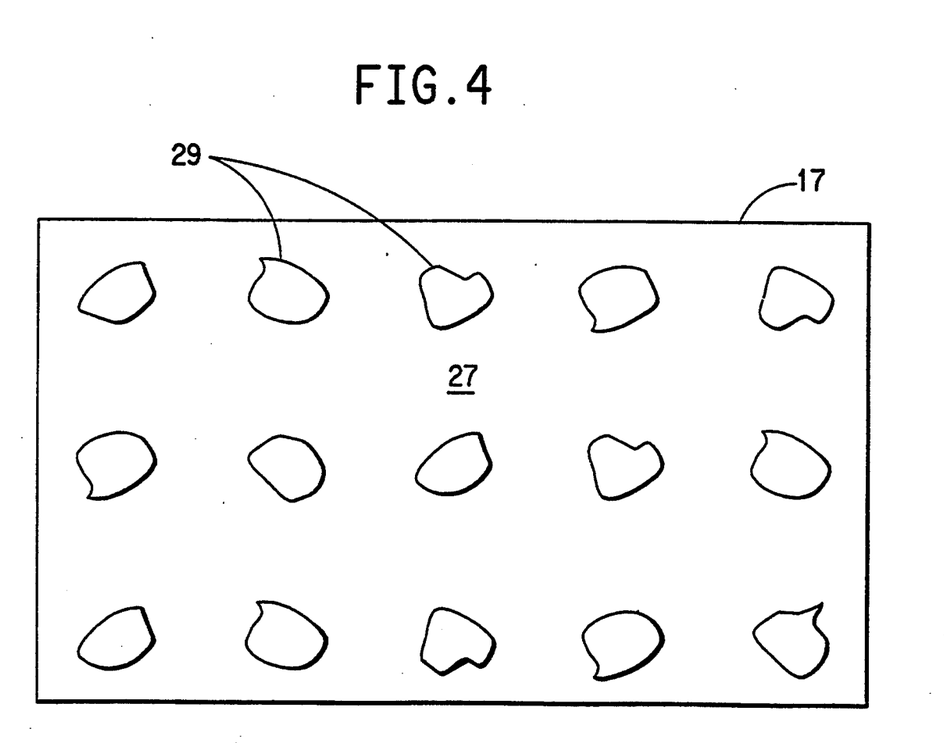
FIG. 4 is a plan view of the product of FIG. 3 with a single particle adhering to each of the tacky areas.

This invention is further illustrated by reference to the product (10) shown in FIG. 1. The product (10) comprises a support (11) including a layer of glass or plastic (13), a tacky nonphotosensitive layer (15), and a photohardenable (photoadhereable) layer (17). The product (10) as shown also has a cover sheet (19) which is removably attached to the photohardenable layer (17) prior to exposure to actinic radiation and is transparent to actinic radiation. The photohardenable layer upon imagewise exposure to actinic radiation adheres to and is removable with the cover sheet only in the exposed areas, represented by areas (23) in FIG. 2. Accordingly, as illustrated in FIG. 2, as the strippable cover sheet (19) is removed after exposure, portions (23) of the photohardenable layer (17) are also removed, resulting in the formation of tacky areas (25) toward the surface (27) of the support (11) which are receptive to particulate material. FIG. 3 shows the product after removal of the cover sheet and the exposed areas of the photohardenable layer (17), including support surface (27) and an array of tacky areas (25). FIG. 4 shows the product of FIG. 3 after flowing particles across the support surface to allow particles (29) to contact the tacky areas and adhere thereto.

More particularly, the Figures may be related to a Negative Cromalin ® C/N system. Negative Cromalin ® C/N reproduces images using a multilayer element comprising a strippable cover sheet (19), a photoadherable layer (17), and a tacky, nonphotosensitive contiguous layer receptive to particulate material, herein referred to as an adhesive layer (15). As supplied, the Negative Cromalin ® C/N generally has another removable bottom cover sheet (not shown) which is initially attached to the tacky layer and is peeled off, and the adhesive layer (15) is affixed to a layer (13) of choice (e.g., a glass slide). The product is then exposed with a pattern of ultraviolet light which makes the photoadherable layer (17) attach to the strippable cover sheet (19) in the light-struck areas. The cover sheet (19) is stripped bringing with it pieces of photoadherable layer (17) corresponding to the light-struck areas. As a result, only adhesive layer (15) remains uncovered on the bottom support layer (13) in the light-struck areas, whereas in the nonlight-struck areas, photoadherable layer (17) remains covering the contiguous adhesive layer (15) and layer (13). When particles are flowed across this surface they do not attach to the remaining photoadherable layer (17) in the nonlight-struck areas but readily attach to the adhesive layer (15) in the light-struck area.

Occasionally, particularly with finer particles, there is a slight tendency for attachment to the background of the photoadherable layer (17). The background can be made less attractive to fine particles by an overall ultraviolet light exposure after cover sheet (19) has been removed. Also there are surface treatments that make (17) less attractive to particles. Usually these extraordinary measures are not needed.

Cover sheet (19) usually is a polyester film and may be surface treated to enhance adhesion to layer (17).

Less adherent cover sheets include polypropylene and silicone-release Mylar ®. If large open tacky areas are present in the image even polypropylene can attach too strongly and silicone-release Mylar ® is better.

For best results with the Cromalin ® Negative Film C/N, the array should be developed by removing the cover sheet after imaging followed by postexposure to make the background less tacky and less easily damaged in handling. To prevent damage or contamination during postexposure a fresh cover sheet can be used on the tacky dot array. For regular tacky dot patterns in Cromalin ® C/N, polypropylene is a preferred replacement cover sheet over the developed tacky dot array because it gives a more uniform looking non-tacky background. Polypropylene does not stick to tacky dots primarily because they are recessed in 3.5 μm deep holes and do not contact the polypropylene except in large open areas.

For surface tacky images as in Positive Cromalin ® and phototackified images, and for above-surface tacky images such as printed adhesive patterns, a cover sheet would intimately contact the adhesive. Accordingly, care should be taken in selecting a protective cover sheet for these embodiments. Silicone-release Mylar ® or the like is a suggested cover sheet material. For above-surface adhesive images, care should also be taken to prevent the cover sheet from crushing and spreading the adhesive pattern.

Photohardenable layers such as layer (17) are generally a combination of polymeric binder and photopolymerizable monomers. Suitable binders include co(-methyl methacrylate/methacrylic acid) and monoethyl ester of poly(methyl vinyl ether/maleic anhydride), each of which may be copolymerized in various proportions. Suitable photopolymerizable monomers include ethylenically unsaturated monomers which have been found useful are those disclosed in Plambeck, U.S. Pat. No. 2,760,863; Cohen and Schoenthaler, U.S. Pat. No. 3,380,831 and Chambers and Woodward U.S. Pat. No. 3,573,918. There may be mentioned as examples dipentaerythritol acrylate (50% tetra and 50% penta), pentaerythritol triacrylate and tetraacrylate, polypropylene glycol (50) ether of pentaerythritol tetraacrylate, polyethylene glycol (200) dimethacrylate, dipentaerythritol triacrylate β-hydroxyethyl ether, polypropylene glycol (550) ether of pentaerythritol tetramethacrylate, pentaerythritol tetramethacrylate, polypropylene glycol (425) dimethacrylate, trimethylolpropane trimethacrylate, and polypropylene glycol (340) ether of trimethylol propane triacrylate. Also useful are epoxy monomers containing ethylene unsaturation, e.g., monomers of the type disclosed in U.S. Pat. No. 3,661,576 and British Patent No. 1,006,587. The binder may be varied widely in its ratio with the monomer but in general it should be in the range of 3:1 to 1:3. The monomer should be compatible with, and may be a solvent for, and/or have a plasticizing action on the binder. The choice and proportions of monomer and binder are made in accordance with the requirements of selective photoadherence. The type and amount of binder is chosen so that in the unexposed state, the surface of the layer (17) is not tacky enough to receive particles and has a lower adhesive force with cover sheet (19) than with adhesive layer (15). The adhesive layer (15) may be a tacky polymer such as a styrene/butadiene or styrene/isoprene block copolymer elastomer or a blend of tacky and nontacky polymers. Suitable tacky polymers include various elastomeric polymers and mixtures thereof having a second order transition temperature of $-10°$ C. or lower which are inherently tacky or will accept tackifying agents and which are nonmigratory into said photoadherent layer and which will impart tackiness to the layer. Rubber type polymers, both natural and synthetic may be used, e.g., isobutylene, Thiokol A, nitrile rubbers, butyl rubber, chlorinated rubbers, polymers of butadiene, isoprene, poly(-vinylisobutylether), and random, teleblock and block copolymers of butadiene or isoprene copolymerized with styrene, and neoprene, silicone elastomers etc., in various proportions. The bottom layer (13) may be a transparent or opaque, colorless or colored, smooth support layer. Preferable materials include glass and polymeric films. Most preferred are glass microscope slides.

Adhesion of adhesive layer (15) to a glass slide support layer (13) is not very much greater than that of photoadherent layer (17) to cover sheet (19) so care must be taken in peeling the cover sheet (19) from the imaged assembly. Generally, a swift 180° peel works the best both in minimizing delamination from the glass slide and giving complete removal of photoadherent layer (17) in the exposed layers.

A characteristic of the product of the present invention is that it greatly simplifies the counting of different solids affixed to a predetermined number of tacky dots on the slide. Grain counting as described by E. N. Cameron (Chapter 9, Ore Microscopy, Wiley, N.Y. 1961) involves the counting of two or more minerals which can be distinguished by their shape, color, etc. Typically, with such grain counting a trained operator has to count at least 300 grains. Having a known number of grains affixed, in accordance with the present invention one needs to count only those minerals which are present as the minor components, thus saving time which can be used to analyze a greater number of grains to reduce the analytical error.

The counting can be done either manually or automatically with machine vision where digitized images obtained with a camera attached to an eyepiece of a microscope are computer analyzed. Here the advantage of the attachment of a single particle per dot is important. For example, if a producer of grass seeds wishes to determine with an automatic analyzer the number of contaminants present, he may program an automatic image analyzer to count everything that doesn't have the shape of a single grass seed as a contaminent. Two grass seeds attached to the same dot may look like a contaminent and be counted as such, thus, overcounting the contaminants in a sample.

The affixing of particles to the tacky dots also has the advantage of uniquely placing them so that they can be found again by simply noting their coordinates. Moreover, a curable resin may be applied over the array of mounted particles and hardened to permanently embed the particles therein so that they can be conveniently sectioned for microscopic analysis of the particle interior.

A characteristic of the product of the present invention is that it is very amenable to automated analysis. A typical automated set up comprises a mounted sample, a microscope, a video camera and an image analyzer.

Automated digital image scanning measures each or all of color, reflectivity, shape and other properties.

An automated counter can be set up to reject multiples i.e., more than one particle attached to an adhesive area, but single mounted particles are preferred.

The analysis can also be done visually (essentially by counting). Typically, a trained operator employs a mounted sample and a microscope. With the method of the present invention, a conventional one-half hour analysis can typically be carried out in less than five minutes.

The counting may be used in conjunction with a standard sample splitting procedure familiar to those dealing with heavy mineral concentrates or crushed ore samples. Typically, an ore sample is carefully split using a microsplitter to obtain a small enough sample to just cover one or two slides. The sample may be applied to the slide using a slide mount holder as described above. A second slide may be used as a cover. Holding the mount with both slides and the sample horizontally, it may be carefully tapped in such a way that the ore grains are affixed to the tacky dots. If there is an excess of ore, the mount may be turned over so that the excess can be affixed to the second slide. This procedure allows for quantitative mounting of a representative sample.

Practice of the invention will become further apparent from the following non-limiting Examples.

EXAMPLES

Example 1

This example illustrates the use of Cromalin ® Positive Film on glass slides to form tacky dots and the attachment of mineral particles to the tacky centers. Cromalin ® Positive Film consists of a tacky, negative-working photopolymer sandwiched between two removable clear cover sheets. In use, one cover sheet is removed and the tacky material is laminated to a substrate. The laminate is exposed to strong ultraviolet light through a patterning phototool; exposed areas become non-tacky. Finally, the second cover sheet is removed revealing a tacky pattern corresponding to the unexposed areas.

Cromalin ® Positive Film SN 556548 (E. I. du Pont de Nemours and Company, Inc., Wilmington, Del.) was laminated to Corning Micro Slides #2948 (Corning Glass Works, Corning, N.Y.) on a coated paper carrier sheet using a laminator at 102° C., a feed rate of 0.8 meters per minute and roll pressure of 30 pounds per square inch. The laminated slides were cut away from the carrier paper, placed in a NuArc FT18V Flip Top Platemaker (NuArc, 4100 W. Grand Ave., Chicago, Ill. 60651) with a 1000 watt mercury lamp, covered with a phototool containing a wide range of dot patterns in regular square screen arrays, put under vacuum, and exposed for one unit. The cover sheet was rapidly peeled off the exposed laminate at a 180° angle and the tacky pattern dusted with an excess of Florida ilmenite mineral powder of particle size 155 to 175 microns and the excess, unattached powder shaken and tapped off. Dots corresponding to 3% dots on a 65 line per inch screen array (68 micron dot diameter and 390 micron center-to-center separation in a square array) were nearly 100% occupied with mineral and about 95% were occupied by single particles.

When mineral particles up to 65 micron were applied to a square array of tacky dots with 37 micron diameter dots and 212 micron center-to-center separation, nearly 100% of the centers were occupied, about 60% of the centers were singly occupied and 40% doubly occupied.

Example 2

This example illustrates the short shelf life of small tacky dots in Cromalin ® Positive Film.

Cromalin ® Positive Film SN 556548 was laminated to Corning Micro Slides #2948 at 105° C. in a Cromalin ® laminator using a carrier paper to convey the slides through the laminator. The slides were separated and placed in the vacuum frame of the NuArc FT18V Flip Top Platemaker, covered with a phototool containing arrays of fine hole patterns, further covered with a filter for ultraviolet light consisting of indium tin oxide coated on 4 mil Cronar ® polyester film with 1100 ohm surface resistance at 1 centimeter, placed under vacuum, and exposed with a 1000 watt mercury lamp for 7 units. At various times after exposure the cover sheets were removed and the tackiness and diameter of the tacky dots checked by toning with fine Cromalin ® toner powder.

Dots corresponding to 1% dots in a 150 line per inch screen started with an initial toned diameter of 18 microns. By aging the image 5 hours and toning, the dot diameter was 8 microns, and after aging 22 hours, no toning took place indicating that all effective tackiness was lost. Dots corresponding to 2% area of 150 line per inch screen started with 25 micron diameter, still toned weakly after 52 hours, and stopped toning after 4 days.

Example 3

This example illustrates the use of Cromatone ® Negative Overlay Film to generate tacky dot arrays for the separate attachment of mineral grains in a nice array. Cromatone ® consists of a 2 mil clear polyester support sheet, a tacky adhesive layer, a photoadherent layer, and a cover sheet. Upon exposure to strong ultraviolet light through a phototool with a dot pattern, the photoadherent layer is made to stick to the cover sheet where struck with light. When the cover sheet is removed, the photoadherent layer stays with the cover sheet in the light struck areas and stays with the tacky adhesive layer in the areas not struck with light. The result is that the adhesive layer is uncovered in the exposed areas creating a tacky pattern.

Cromatone ® Negative Overlay Film SN 031372 (E. I. du Pont de Nemours and Company, Inc., Wilmington, Del.) was exposed through a phototool with a variety of dot arrays to 5 units from a 1000 watt mercury lamp in a NuArc FT18V Flip Top Platemaker. The cover sheet was ripped off rapidly at a 180° angle and the tacky pattern dusted with an excess of Florida ilmenite mineral powder of particle size 155 to 175 microns and the excess, unattached powder shaken and tapped off. Dots corresponding to 3% dots on a 65 line per inch screen (68 micron tacky dot diameter and 390 micron center-to-center separation in a regular square array) were nearly 100% occupied with single mineral particles in a regular square array.

Example 4

This example illustrates the use of Cromalin ® Negative Film C/N on glass slides to make tacky dots in a regular square array and the attachment of crystals of an organic compound (sucrose) to the tacky centers. Cromalin ® Negative Film C/N consists of removable cover sheet, a tacky adhesive layer, a photoadherent layer, and another removable cover sheet. The cover sheet next to the adhesive is removed and the adhesive laminated to a substrate. The laminate is exposed to strong ultraviolet light through a phototool with a dot pattern. The photoadherent layer is made to stick to the adjacent cover sheet where struck with light. When the cover sheet is removed, the photoadherent layer stays with the cover sheet in the light struck areas and stays with the tacky adhesive in the areas not struck with light. The result is that the adhesive layer is uncovered in light struck areas creating a tacky pattern.

Cromalin ® Negative Film C/N, SN 529818 (E. I. du Pont de Nemours and Company, Inc., Wilmington, Del.) was laminated to Corning Single Frosted Micro Slides #2948 (Corning Glass Works, Corning, N.Y.) on a coated paper carrier sheet using a Cromalin ® Laminator at 108° C. and 6 feet per minute. The laminated slides were cut away from the carrier sheet, placed in a NuArc FT18V Flip Top Platemaker under vacuum, and exposed through a phototool of the desired dot pattern to 10 units from a 1000 watt mercury lamp. The cover sheet was ripped off rapidly at a 180° angle and the tacky pattern dusted with Domino granulated cane sugar and the excess, unattached granules shaken and tapped off. With 150 micron tacky dots in a regular square array with 1000 microns center-to-center, sugar crystals attached in a nice array with nearly 100% of centers occupied mostly with single large crystals ranging from 200 to 400 microns in width. Some fines were noted which interfered with attachment of the larger crystals at a few centers. With 300 micron tacky dots and 2000 micron spacings, sugar crystals singly and multiply populated the centers about equally.

Example 5

This example illustrates the use of Cromalin ® Negative Film C/N on glass slides to form square arrays of tacky dots and the attachment of inorganic crystals, sodium chloride, to the tacky centers.

The steps of Example 4 were repeated to make tacky arrays. Excess Morton Iodized Salt was dusted on the arrays and the excess, unattached grains shaken and tapped off. With 150 micron tacky dots in a square array 1000 microns center-to-center, salt only populated 34% of the centers. With 300 micron tacky dots and 2000 micron separation, large salt crystals attached to 85% of the centers, 55% single grains per center but 30% of centers had multiple populations of large crystals. The salt crystals are similar in size to the sugar crystals of Example 4, mostly 200 to 400 microns in width, but are cubic with larger faces, are covered with a fine anticaking powder, and have a higher specific gravity. About 80% of the salt crystals are more than 300 microns wide. The salt crystals could span the tacky holes 150 microns in width without touching the adhesive since the adhesive is slightly recessed by 4 microns.

Example 6

This example illustrates the stability of the latent dot pattern image in Cromalin ® Negative Film C/N.

Cromalin ® Negative Film C/N was laminated at room temperature to a coated white paper and exposed as in Example 4 to a 2% dot in a 150 line per inch square array. This corresponds to 25 micron wide holes. The exposed pattern was stored in the dark with the cover sheet still next to the photoadherable layer. Periodically a sample was removed, peeled, and toned with a fine particle Cromalin ® toner to determine whether the latent image will still peel apart properly revealing a tacky dot pattern and whether the dot size changes. After ten months storage, the cover sheet was ripped off rapidly at 180° and toned to give a toned image consisting of the same 2% dot pattern as obtained from a fresh image. No change was noted in the latent image over 10 months.

Example 7

This example illustrates the use of different tacky dot sizes to capture different ranges of particles with a preference for either one or two particles per center. Tacky dots were generated using Cromalin ® Negative Film C/N on glass slides.

The steps of Example 4 were used to make a variety of tacky dot square arrays on glass slides with a variety of center-to-center separations. Each was tested with a series of narrow size ranges of mineral particles to determine what size particles would predominantly singly or doubly populate each size tacky center. The particles were largely rounded irregularly shaped particles, not flat. The results are summarized in Table I.

TABLE I

| Dot Size μm/ Spacing μm | Particle Size Range μm | % Doubles | % Opens |
|---|---|---|---|
| 25/500 | 21–44 | | |
| | above 44 | | |
| 40/500 | 44–53 | fair | nil |
| | 53–63 | few | nil |
| | above 63 | few | nil |
| 50/500 | 44–53 | 50% | 0% |
| | 53–63 | 40% | 0% |
| | 63–74 | 24% | 0% |
| | 74–88 | 5% | 0% |
| | 88–105 | 2% | 0% |
| | 105–125 | 0% | 7% |
| | 125–150 | 0% | 21% |
| | above 150 | | |
| 75/500 | 77–88 | 42% | 0% |
| | 88–105 | 16% | 0% |
| | 105–125 | 7% | 2% |
| | 125–150 | 2% | trace |
| | 150–175 | 2% | 2% |
| | 175–250 | 2% | 2% |
| | above 250 | (a) | 20% |
| 100/1000 | 105–125 | 49% | 0% |
| | 125–150 | 25% | 0% |
| | 150–175 | 8% | 0% |
| | 175–250 | 9% | 1% |
| | above 250 | 1% | 4% |

(a) bridging

A high number at singly occupied sites together with a low number of vacant sites (opens) is typical of runs where the particle size is from about 2 to 3 times the dot size. A high number of doubly occupied sites is typical of runs where the particle size is comparable to the dot size.

Example 8

This Example illustrates the use of different tacky dot sizes to capture various size ranges of rounded, smooth sand particles with a preference for one particle attached per center. Tacky dots were generated using Cromalin ® Negative Film C/N on glass slides.

The steps of Example 4 were used to make tacky dot square arrays on glass slides with a variety of tacky dot sizes and center-to-center separations. Each was tested with a series of narrow size ranges of particles to determine what size particles would predominantly singly populate each size tacky center.

Florida ilmenite sand was separated into several particle size fractions using standard sieves and mounted on appropriate sized tacky centers. The particles were largely rounded, smooth, irregularly shaped particles, not flat or rough. The results are summarized in Table II.

TABLE II

| Particle Size μm | Tacky array size μm dots/separation | Particle Attachment per Center | | |
|---|---|---|---|---|
| | | single | double | vacant |
| about 355 | 150/1000 | 98.0% | 0.3% | 1.7% |
| 250–355 | 150/1000 | 100% | 0 | 0 |
| 180–250 | 100/1000 | 99.5% | 0.5% | 0 |
| 150–180 | 75/500 | 100% | 0 | 0 |
| 125–150 | 50/500 | 97.7% | 0.4% | 1.9% |
| 75–125 | 50/500 | 99.2% | 0 | 0.8% |

Example 9

This Example illustrates the use of different tacky dot sizes to capture various size ranges of crushed mineral particles with rough irregular angular shapes with a preference for one particle attached per center. Tacky dots were generated using Cromalin ® Negative Film C/N on glass slides.

The steps of Example 4 were used to make tacky dot square arrays on glass slides with a variety of tacky dot sizes and center-to-center separations. Each was tested with a series of narrow size ranges of particles to determine what size particles would predominantly singly populate each size tacky center.

Crushed Richards' Bay slag, Richard's Bay, South Africa, was separated into several particle size fractions using standard sieves and mounted on appropriate sized tacky centers. The particles were largely angular, rough, irregularly shaped particles with some flat faces, not rounded or smooth. The results are summarized in Table III.

TABLE III

| Particle Size μm | Tacky array size μm dots/separation | Particle Attachment per Center | | |
|---|---|---|---|---|
| | | single | double | vacant |
| about 355 | 150/1000 | 95.1% | 2.3% | 2.6% |
| 250–355 | 100/1000 | 90.5% | 8.2% | 1.3% |
| 180–250 | 75/500 | 89.6% | 10.0% | 0.4% |
| 150–180 | 50/500 | 90.3 | 6.5% | 3.2% |
| 125–150 | 41/500 | 92.5% | 6.3% | 1.3% |
| 75–125 | 41/500 | 83.3% | 16.2 | 0.5% |

Example 10

This example illustrates the use of a masked sample holder to mount a glass slide covered with an array of tacky dots such that a reproducible number of particles can be attached, mostly one particle per tacky center. This further illustrates how the average weight per attached particle is determined for three different materials. This is used in determining the weight percent of each component in a mixture of the three different particles. A procedure is described that gives representative attachment of rounded ilmenite and irregular rough crushed RBS particles from a 1:1 weight mixture and also does fairly well in attaching hexagonal prisms of sodium sulfite, which has a much lower specific gravity than ilmenite and RBS, from a 1:1:1 weight mixture with ilmenite and RBS.

A sample holder was made from a 3×6 inch metal sheet, 0.07 inch thick, by cutting a 0.75×2.75 inch window in the middle, surrounding the perimeter of the window with a contact adhesive and attaching a 0.007 inch thick, 3×6 inch polyester film over the metal sheet. A 0.70×1.95 inch window was cut in the polyester film above the window in the sheet metal such that a border of polyester film overhangs the perimeter of the metal window. Guide stops were taped on the polyester so that 1×3 inch slides would be positioned over the polyester window so that the frosted end (if present) would not be over the window and the entire perimeter of the slide would be masked from particle attachment to some extent.

The window opposite the polyester frame side was covered with glass, taped to the frame, and placed on a level surface with the glass side down. Particle samples were poured into the open window to rest in the cavity formed by the frame and glass bottom. Cromalin ® Negative Film C/N was laminated to glass microscope slides as in Example 4, exposed to an array pattern of 50 micron dots with a 500 micron center-to-center separation, developed by removing the cover sheet, and weighed. The slide was then mounted in the sample holder Cromalin ® side down over the polyester window, and locked in place with a cover and clamps over the metal frame. The claimed assembly was rotated upside down spilling the particle sample onto the tacky dot array inside the holder. The polyester frame limited attachment to a 98×35 array or 3430 centers. The assembly was tipped, rocked, and shaken until essentially all centers were occupied. The assembly was returned to its original position with the glass slide on top, tapped gently to remove loose particles from the slide, and the slide removed and weighed to determine attached particle weight.

Florida ilmenite and Richard Bay Slag were sieved and the material that passed through an 80 mesh screen but not through 100 mesh, particle sizes of 150 to 180 microns, were mounted and weighed by the above procedure. The number of centers occupied were visually counted using an optical microscope at 10 to 50× magnification and the number of singly and doubly occupied centers counted so that a total number of mounted particles determined.

|  | Size (microns) | Sites | Particles | Grams/Particle × 10⁶ |
|---|---|---|---|---|
| Florida ilmenite | 150–180 | 3347 | 3347 | 10.82 |
|  |  | 3425 | 3425 | 10.77 |
| Richards Bay Slag | 150–180 | 3355 | 3774 | 9.75 |
|  |  | 3425 | 3892 | 9.66 |

The sample holder was modified by removing the plain glass cover. Cromalin ® Positive Film was laminated to glass microscope slides as in Example 1, exposed in an array of 50 micron tacky dots with 500 micron center-to-center separations, the cover sheet removed, mounted on the polyester frame side of the sample holder, clamped in place, and placed on a level surface with the slide on the bottom. A mixture of 1.00 grams each of 150-180 micron Ilmenite and Richards Bay Slag was gently poured evenly onto the entire surface of the slide in the holder. The holder was rocked until nearly all tacky sites were occupied then turned over, the excess dumped, and the slide gently tapped to remove any loose particles. For one sample and tacky dot array, the rocking motion was side-to-side and the particles moved no more than 0.75 inch back and forth. For another, the rocking motion was end-Go-end and particles could move back and forth 2.75 inches. The populations of attached species was counted. All centers with any ilmenite (maximum of one) were counted as a site for initial ilmenite attachment. Centers with one or more RBS were counted as centers for initial RBS attachment. The number of initial attachments by ilmenite was multiplied by $10.8 \times 10^{-6}$ to give the relative weight of ilmenite in the sample. The number of initial attachments of RBS was multiplied by $9.7 \times 10^{-6}$ to give the relative weight of RBS in the sample. Side-to-side rocking gave the best results.

|  | (theory 50%) weight % ilmenite | (theory 50%) weight % RBS |
|---|---|---|
| side-to-side rock | 52.0% | 48.0% |
| end-to-end rock | 57.0% | 43.0% |

Other mixtures were similarly analyzed.

| Initial Mixture wt % | | Attached | Attached |
|---|---|---|---|
| ilmenite | RBS | ilmenite wt % | RBS weight % |
| 5.0% | 95.0% | 5.7% | 94.3% |
| 95.0% | 5.0% | 94.0% | 6.0% |

A more complicated mixture was similarly analyzed which added low specific gravity, flat crystals, hexagonal prisms of sodium sulfite. First, the weight per particle of sodium sulfite was determined.

Sodium sulfite, certified ACS, anhydrous (Fisher Scientific, Fairlawn, N.J. 07410) was sieved into fractions and the 150 to 180 micron size range particles mounted on a weighed array of 50 micron tacky dots with 500 micron center-to-center separation in Cromalin ® Positive Film. A total of 3566 particles were attached (3303 as singles), weighed 0.0267 gram for a weight per particle of $7.49 \times 10^{-6}$ gram.

A 1:1:1 mixture, 0.200 grams each, of low density hexagonal prisms, sodium sulfite, rounded ilmenite, and rough irregular blocky crushed RBS was attached to Cromalin ® Positive Film tacky dot array as in the above 1:1 mixture using the side-to-side flowing motion until all sites seemed occupied. Sodium sulfite behaves more like ilmenite than RBS in attachment characteristics. All sites with ilmenite were counted as initial ilmenite attachment, all with sodium sulfite as initial sodium sulfite attachment. The number of initial attachments for each particle type was multiplied by the weight per particle of that material to determine the relative weight of each particle type in the sample. Only 30% of the sites were counted.

|  | Initial Attachments counted | Attached weight $10^{-6}$ g | weight % | theory |
|---|---|---|---|---|
| RBS | 300 | 2910 | 32.5% | 33.3% |
| ilmenite | 209 | 2257 | 25.2% | 33.3% |
| Sodium sulfite 505 | 505 | 3788 | 42.3% | 33.3% |

In spite of wide shape and density differences, a fairly representative sample can be attached to the tacky dot arrays for easy counting. For more accurate results, all particles of a representative sample could be attached, counted and multiplied by the weight per particle.

Particular embodiments of the invention are included in the examples. Other embodiments will become apparent to those skilled in the art from a consideration of the specification or practice of the invention disclosed herein. It is understood that modifications and variations may be practical without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for mounting free-flowing particles in an array having at least 50% singly or doubly mounted particles, comprising the steps of: (a) providing a support surface having an array of tacky areas which have a size and bonding strength suitable for adhesion of either one or two of said particles; and (b) flowing said particles across the support surface to allow particles to contact the tacky areas and adhere thereto.

2. The process of claim 1 wherein the tacky areas have a size and bonding strength suitable for adhesion of two of said particles.

3. The process of claim 1 wherein the tacky areas have a size and bonding strength suitable for adhesion of one of said particle.

4. The process of claim 3 wherein the size of each tacky area is less than the particle size and the tacky areas are separated, center to center, by at least about two times the longest particle dimension.

5. The process of claim 1 wherein the tacky areas are provided by photoimaging.

6. The process of claim 1 wherein the array of tacky areas is formed using the steps of:

(1) providing an actinic radiation sensitive multilayer product comprising (i) a strippable cover sheet, (ii) a photoadherable layer, (iii) a tacky, nonphotosensitive contiguous layer receptive to particulate material, and (iv) a support layer, wherein said tacky layer is attached between said support layer and said photoadherable layer and the cover sheet is removably attached to the photoadherable layer prior to exposure to actinic radiation and is adhered to areas of the photoadhereable layer which are exposed to actinic radiation;

(2) exposing the radiation sensitive multilayer element to actinic radiation imagewise in the array pattern, and (3) stripping off the cover sheet removing the photoadherable layer in the areas exposed by the actinic radiation.

7. The process of claim 6 wherein the strippable cover sheet is a polymeric film which is transparent to actinic radiation, the photoadherable layer is a combination of polymeric binder and photopolymerizable monomers, and the tacky layer is a styrene/butadiene or styrene/isoprene block copolymer elastomer, or a blend thereof with nontacky polymers.

8. The process of claim 6 where the support layer is a glass microscope slide.

9. The process of claim 6 where the support layer is a polymeric film.

10. A product for mounting free-flowing particles in an array, comprising: a support having a support surface with an array of tacky areas which have a size and bonding strength suitable for adhesion of either one or two of said particles.

11. The product of claim 10 wherein the support comprises rigid transparent glass.

12. The product of claim 10 wherein the tacky areas are provided by photoimaging.

13. The product of claim 10 comprising an actinic radiation sensitive multilayer combination comprising (i) a strippable cover sheet, (ii) a photoadherable layer, (iii) a tacky, nonphotosensitive contiguous layer receptive to particulate material, and (iv) a support layer, wherein said tacky layer is attached between said support layer and said photoadherable layer and the cover sheet is removably attached to the photoadherable layer prior to exposure to actinic radiation and is adhered to areas of the photoadherable layer which are exposed to actinic radiation.

14. The product of claim 10 which is formed using process steps comprising (1) providing an actinic radiation sensitive multilayer product comprising (i) a strippable cover sheet, (ii) a photoadherable layer, (iii) a tacky, nonphotosensitive contiguous layer receptive to particulate material, and (iv) a support layer, wherein said tacky layer is attached between said support layer and said photoadherable layer and the cover sheet is removably attached to the photoadherable layer prior to exposure to actinic radiation and is adhered to areas of the photoadhereable layer which are exposed to actinic radiation; (2) exposing the radiation sensitive multilayer element to actinic radiation imagewise in the array pattern; and (3) stripping off the cover sheet removing the photoadherable layer in the areas exposed by the actinic radiation.

15. The product of claim 10 wherein the tacky areas are spaced so that after attachment of particles, no particles attached to a tacky area touches to a particle attached to any other tacky area.

16. The product of claim 10 wherein the tacky areas have a size and bonding strength suitable for adhesion of only one of said particles.

17. The product of claim 16 wherein the tacky areas are spaced to avoid a particle which is retained on one tacky area from touching a particle retained on another tacky area.

18. The product of claim 17 wherein the tacky areas have a size and bonding strength suitable for mounting free-flowing particles having a particle size between 5 $\mu$m and 2000 $\mu$m.

19. The product of claim 18 wherein the tacky areas have a size and bonding strength suitable for mounting ore grains.

* * * * *

UNITED STATES PATENT AND TRADEMARK OFFICE
CERTIFICATE OF CORRECTION

PATENT NO. : 5,356,751

DATED : October 18, 1994

INVENTOR(S) : Allan Cairncross and Ulrich Klabunde

It is certified that error appears in the above-identified patent and that said Letters Patent is hereby corrected as shown below:

Column 2, line 18:

Change "analysis by microscopy are generally, transparent and"

to -- analysis by microscopy are generally transparent and --

Column 10, lines 34-35:

Change "Cromalin® Positive Film consists of a tacky, negative working photopolymer sandwiched between two"

to -- Cromalin® Positive Film consists of a tacky photopolymer sandwiched between two --

UNITED STATES PATENT AND TRADEMARK OFFICE
CERTIFICATE OF CORRECTION

PATENT NO. : 5,356,751

DATED : October 18, 1994

INVENTOR(S) : Allan Cairncross and Ulrich Klabunde

It is certified that error appears in the above-identified patent and that said Letters Patent is hereby corrected as shown below:

Column 14, Table II, line 11, first column:

Change "about 355"

to -- above 355 --

Column 14, Table III, line 43, first column:

Change "about 355"

to -- above 355 --

Column 15, line 25:

Change "the metal frame. The claimed assembly was rotated"

to -- the metal frame. The clamped assembly was rotated --

UNITED STATES PATENT AND TRADEMARK OFFICE
CERTIFICATE OF CORRECTION

PATENT NO. : 5,356,751

DATED : October 18, 1994

INVENTOR(S) : Allan Cairncross and Ulrich Klabunde

It is certified that error appears in the above-identified patent and that said Letters Patent is hereby corrected as shown below:

Column 15, line 60:

Change "grams each of 150-180 micron Ilmenite and Richards"

to -- grams each of 150-180 micron ilmenite and Richards --

Column 16, line 1:

Change "end-Go-end and particles could move back and forth"

to -- end-to-end and particles could move back and forth --

Column 17, line 6:

Change "may be practical without departing"

to -- may be practiced without departing --

UNITED STATES PATENT AND TRADEMARK OFFICE
CERTIFICATE OF CORRECTION

PATENT NO. : 5,356,751

DATED : October 18, 1994

INVENTOR(S) : Allan Cairncross and Ulrich Klabunde

It is certified that error appears in the above-identified patent and that said Letters Patent is hereby corrected as shown below:

Column 17, line 26:

Change "of one of said particle."

to -- one of said particles. --

Column 18, line 43:

Change "to a tacky area touches to a particle"

to -- to a tacky area touches a particle --

Signed and Sealed this

Fourth Day of July, 1995

Attest:

BRUCE LEHMAN

Attesting Officer

Commissioner of Patents and Trademarks